United States Patent
Haley et al.

(10) Patent No.: US 6,914,068 B2
(45) Date of Patent: *Jul. 5, 2005

(54) THIAZOLO[4,5-B]PYRIDINES AS FUNGICIDES

(75) Inventors: Gregory J. Haley, Newtown, PA (US); Keith D. Barnes, Newtown, PA (US); William W. Wood, Pennington, NJ (US); Yulin Hu, Plainsboro, NJ (US); Salvatore Cuccia, deceased, late of Lawrenceville, NJ (US); by Kathryn C. Ferguson, legal representative, Lawrenceville, NJ (US); Henry Van Tuyl Cotter, Ewing, NJ (US); Andreas Gypser, Mannheim (DE); Anja Schwögler, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 591 days.

This patent is subject to a terminal disclaimer.

(21) Appl. No.: 09/902,783

(22) Filed: Jul. 12, 2001

(65) Prior Publication Data

US 2003/0083311 A1 May 1, 2003

(51) Int. Cl.$^7$ .......................................... A61K 31/435
(52) U.S. Cl. .................................. 514/301; 514/63
(58) Field of Search .................... 514/301, 63

(56) References Cited

U.S. PATENT DOCUMENTS 5,504,082 A    4/1996   Kawakita et al. ............ 514/234
5,616,581 A    4/1997   Kawakita et al. ............ 514/234

FOREIGN PATENT DOCUMENTS

| EP | 0 405 976 | 1/1991 |
|---|---|---|
| EP | 1 000 946 | 5/2000 |
| JP | 6 220727 | 9/1987 |
| WO | WO 93/24480 | 12/1993 |

*Primary Examiner*—Bernard Dentz
(74) *Attorney, Agent, or Firm*—Keil & Weinkauf

(57) ABSTRACT

A method for controlling harmful fungi, which comprises treating the fungi or the materials, plants, the soil or the seed to be protected against fungal attack and/or animal pests with an effective amount of at least one thiazolo[4,5-b]pyridine of the formula I:

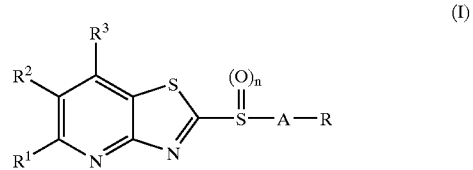

in which n is 0, 1 or 2, the substituents $R^1$, $R^2$, $R^3$, have the following meanings:

$R^1$, $R^2$, $R^3$: independently of one another are: hydrogen, halogen, $C_1$–$C_4$-alkyl, $C_1$–$C_4$-alkoxy, $C_1$–$C_4$-haloalkyl, $C_1$–$C_4$-alkoxy -$C_1$–$C_4$-alkyl or phenyl which may be unsubstituted or carry 1, 2, 3 or 4 substituents which are selected, independently of one another, from halogen, nitro, cyano, alkyl, alkoxy, $OCHF_2$ or $CF_3$; and wherein A and R are as defined in claim 1.

12 Claims, No Drawings

THIAZOLO[4,5-B]PYRIDINES AS FUNGICIDES

The present invention relates to novel thiazolo[4,5-b] pyridines and a method for controlling harmful fungi.

Thiazole compounds, wherein the thiazole ring is fused to a 6 membered aromatic ring have several times been described in the literature as pharmaceutically active compounds. For example, EP-A 405967 discloses fused azolopyridines which carry an organic thio radical or an organic sulfinyl radical on the five membered heterocycle. WO 93/24480 discloses several azolobenzenes and azolopyridines, which carry a 2-pyridylmethylthio radical or a 2-pyridylmethylsulfinyl radical, to have an antibacterial effect against *Heliobacter pylori*. Similar compounds are known from JP 62-(207271 to be useful as antiulcer agents.

WO 97/28128 discloses 6-bromo-2-methylthio-thiazolo [4,5-b]pyridine and 6-bromo-2-methylsulfonyl-thiazolo[4, 5-b]pyridine as intermediates in the preparation of novel inhibitors for the enzyme oxido squalene cyclase.

EP-A 1000946 describes the pesticidal and parasitical use of several 2-(substituted thio)thiazolo[4,5-b]pyridines.

So far, no thiazolo[4,5-b]pyridines have been described, which are useful as fungicides.

In principle, there is a constant need for novel fungicides to be provided, in order to broaden the activity spectrum and to circumvent a possible formation of resistance against the known fungicides.

It is an object of the present invention to provide a new method for combatting harmful fungi and also new compounds which are useful for controlling harmful fungi.

We have found that this object is surprisingly achieved by thiazolo[4,5-b]pyridines of the formula I defined below.

Therefore, the present invention relates to a method for controlling harmful fungi, which comprises treating the fungi or the materials, plants, the soil or the seed to be protected against fungal attack and/or animal pests with an effective amount of at least one thiazolo[4,5-b]pyridine of the formula I:

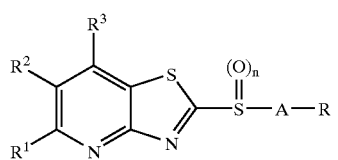

(I)

in which the substituents $R^1$, $R^2$, $R^3$, A and the index n have the following meanings:

$R^1$, $R^2$, $R^3$: independently of one another are: hydrogen, halogen, $C_1$–$C_4$-alkyl, $C_1$–$C_4$-alkoxy, $C_1$–$C_4$-haloalkyl, $C_1$–$C_4$-alkoxy-$C_1$–$C_4$-alkyl or phenyl which may be unsubstituted or carry 1, 2, 3 or 4 substituents which are selected, independently of one another, from halogen, nitro, cyano, alkyl, alkoxy, $OCHF_2$ or $CF_3$;

n: 0, 1 or 2;

R: hydrogen, cyano, halogen, $C_1$–$C_6$-alkyl, $C_1$–$C_4$-haloalkyl, $C_1$–$C_4$-alkoxy, $C_2$–$C_4$-alkenyl, $C_2$–$C_4$-haloalkenyl, $C_2$–$C_4$-alkinyl, $C_2$–$C_4$-haloalkinyl, cyano-$C_1$–$C_4$-alkyl, $C_1$–$C_4$-alkoxy-$C_1$–$C_4$-alkyl, $C_3$–$C_8$-cycloalkyl, tris($C_1$–$C_4$-alkyl)silyl, tris($C_1$–$C_4$-alkyl) silyloxy, $COR^4$, $COOR^5$, $CONR^6R^7$, $S(O)_kR^8$, phenyl, phenoxy, a 5 or 6 membered heterocycle, which has 1, 2, or 3 heteroatoms being selected from O, S and N, and which may be saturated, unsaturated or aromatic, wherein phenyl, phenoxy and the heterocycle, independently of each other, may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$; wherein k is 0, 1 or 2;

$R^4$ is hydrogen, $C_1$–$C_6$-alkyl, phenyl and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

$R^5$ is $C_1$–$C_6$-alkyl, $C_1$–$C_4$-alkoxy-$C_1$–$C_4$-alkyl, phenyl and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

$R^6$,$R^7$ independently from one another are hydrogen, $C_1$–$C_6$-alkyl, $C_1$–$C_4$-alkoxy-$C_1$–$C_4$-alkyl, phenyl, and phenyl-$c_1$–$C_4$-alkyl, wherein phenyl and phenyl-$C_1$–$C_4$-alkyl may carry 1, 2, 3 or 4 substituents on the phenyl ring, which are selected, independently of one another, from halogen, nitro, cyano, $C_1$–$C_4$-alkyl, $C_1$–$C_4$-alkoxy, $OCHF_2$ or $CF_3$; or may together form a 5- or 6-membered heterocycle, which may additionally to the nitrogen atom may have 1 or 2 further heteroatoms selected from N, O or S;

$R^8$ is $C_1$–$C_6$-alkyl, $C_1$–$C_4$-haloalkyl, phenyl, and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

A: $C_1$–$C_4$-alkylene; or

A-R: may together be dihalomethyl, trihalomethyl, $C_3$–$C_8$-cycloalkyl, $C_2$–$C_4$-alkenyl, $C_2$–$C_4$-haloalkenyl, $C_5$–$C_8$-cycloalkenyl or a 5 or 6 membered heterocycle, which has 1, 2, or 3 heteroatoms being selected from O, S and N, which may be saturated, unsaturated or aromatic, and which may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$, wherein cycloalkyl and cycloalkenyl, may independently carry 1, 2, 3 or 4 substituents, which are selected, independently of one another, from halogen and $C_1$–$C_4$-alkyl, and/or may contain a carbonyl or thiocarbonyl ring member;

and/or at least one agriculturally acceptable salts thereof.

The invention also relates to thiazolo[4,5-b]pyridine compounds of the formula I as defined above, except:

2-methylsulfonyl-thiazolo[4,5-b]pyridine,
2-methylsulfonyl-6-bromo-thiazolo[4,5-b]pyridine,
2-methylthio-6-bromo-thiazolo[4,5-b]pyridine,
2-[(methoxycarbonyl)methylsulfinyl]thiazolo[4,5-b] pyridine,
2-[(methoxycarbonyl)methylsulfinyl]-6-trifluoro-thiazolo [4,5-b]pyridine,
2-[(methoxycarbonyl)methylthio]-6-trifluoro-thiazolo[4,5-b]pyridine, and
2-[(methoxycarbonyl)methylthio]thiazolo[4,5-b]pyridine,
2-[(ethoxycarbonyl)methylthio]thiazolo[4,5-b]pyridine, 2-[(4,4,3-trifluoro-3-butenyl)thio]thiazolo[4,5-b]pyridine
2-[(2-propen-1-yl)thio]thiazolo[4,5-b]pyridine,
2-[(cycloproplymethyl)thio]thiazolo[4,5-b]pyridine,
2-[1-(ethoxycarbonyl)ethylthio]thiazolo[4,5-b]pyridine,
2-[(bromodifluoromethyl)thio]thiazolo[4,5-b]pyridine,
2-[(difluoromethyl)thio]thiazolo[4,5-b]pyridine, and
2-[(2,2,2-trifluoroethyl)thio]thiazolo[4,5-b]pyridine.

The invention furthermore relates to agricultural formulations, preferably in the form of a powder, suspension, dispersion, emulsion, emulsion concentrate, oil dispersion, paste, dust, a directly sprayable solution, a material for spreading, or in the form of granules, which comprises at least one thiazolo[4,5-b]pyridine compound of the formula I and/or at least one agriculturally acceptable salt thereof and at least one agriculturally acceptable carrier, which may be liquid or solid.

In the substituents, the thiazolo[4,5-b]pyridines of the formula I may have one or more centers of chirality, in which case they are present as mixtures of enantiomers or diastereomers. The present invention provides both the pure enantiomers or diastereomers and mixtures thereof.

Suitable agriculturally useful salts are especially the salts of those counterions which do not have any adverse effect on the herbicidal action of the thiazolo[4,5-b]pyridines I. Preferred agriculturally usefull salts are selected from the acid addition salts of the thiazolo[4,5-b]pyridines I.

Preferred anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and also the anions of $C_1$–$C_4$-alkanoic acids, preferably formate, acetate, propionate and butyrate. They can be formed by reacting thiazolo[4,5-b]pyridines I with an acid of the corresponding anion, preferably of hydrochloric acid, hydrobromic acid, sulfuric acid, phosphoric acid or nitric acid.

The organic moieties mentioned in the definitions of the radicals A, R, $R^1$ to $R^8$ or as radicals on cycloalk(en)yl, phenyl or heterocyclic rings are—like the term halogen—collective terms for individual listings of the individual group members. All carbon chains, i.e. all alkyl, haloalkyl, alkoxy, haloalkoxy, alkylsulfinyl, haloalkylsulfinyl, alkylsulfonyl, haloalkylsulfonyl, alkenyl, haloalkenyl, alkynyl and haloalkynyl groups, and the corresponding moieties in larger groups, such as alkoxycarbonyl, alkoxycarbonylalkyl, etc., can be straight-chain or branched, where the prefix $C_n$-$C_m$ indicates in each case the possible number of carbon atoms in the group. Halogenated substituents preferably carry one, two, three, four or five identical or different halogen atoms. The term halogen represents in each case fluorine, chlorine, bromine or iodine. Further examples of meanings are:

$C_1$–$C_4$-alkyl and the alkyl moieties of $C_1$–$C_4$-alkoxy, $C_1$–$C_4$-alkylthio, $C_1$–$C_4$-alkylamino, di-$C_1$–$C_4$-alkylamine or $C_1$–$C_4$-alkylcarbonyloxy: saturated, straight-chain or branched hydrocarbon radicals having 1 to 4 carbon atoms, specifically methyl, ethyl, propyl, 1-methylethyl, butyl, 1-methylpropyl, 2-methylpropyl, 1,1-dimethylethyl;

$C_1$–$C_6$-alkyl: saturated, straight-chain or branched hydrocarbon radicals having 1 to 6 carbon atoms, for example $C_1$–$C_4$-alkyl as mentioned above or pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_4$-alkylene: methylene, 1,1-ethylene, 1,2-ethylene, 1,1-propylene, 1,2-propylene, 2,2-propylene, 1,3-propylene, 2-methyl-1,2-propylene, 2-methyl-1,3-propylene, 1,1-butylene, 1,2-butylene, 1,3-butylene, 1,4-butylene, 2,2-butylene, or 2,3-butylene;

dihalomethyl: methyl which carrys 2 halogenatoms, e.g. dichloromethyl, difluoromethyl, chlorofluoromethyl, trihalomethyl: methyl which carrys 3 halogenatoms, e.g. trichloromethyl, trifluoromethyl, dichlorofluoromethyl, chlorodifluoromethyl, bromodifluoromethyl;

$C_1$–$C_4$-haloalkyl and the haloalkyl moieties of $C_1$–$C_4$-haloalkoxy: straight-chain or branched alkyl groups having 1 to 4 carbon atoms (as mentioned above), where the hydrogen atoms in these groups may be partially or fully replaced by halogen atoms as mentioned above, especially $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$–$C_4$-alkoxy: $OCH_3$, $OC_2H_5$, n-propoxy, $OCH(CH_3)_2$, n-butoxy, $OCH(CH_3)$—$C_2H_5$, $OCH_2$—$CH(CH_3)_2$ or $OC(CH_3)_3$, preferably $OCH_3$, $OC_2H_5$, or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e. for example $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_4$-alkoxy-$C_1$–$C_4$-alkyl: $C_1$–$C_4$-alkyl which is substituted by $C_1$–$C_4$-alkoxy as mentioned above, i.e. for example $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)-propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methyl-propoxy)propyl, 3-(2-methylpropoxy)propyl, 3-(1,1-dimethyl-ethoxy)propyl, 2-(methoxy)butyl, 2-(ethoxy)butyl, 2-(n-propoxy)butyl, 2-(1-methylethoxy)butyl, 2-(n-butoxy)-butyl, 2-(1-methylpropoxy)butyl, 2-(2-methylpropoxy)butyl, 2-(1,1-dimethylethoxy)butyl, 3-(methoxy)butyl, 3-(ethoxy)-butyl, 3-(n-propoxy)butyl, 3-(1-methylethoxy)butyl, 3-(n-butoxy)butyl, 3-(1-methylpropoxy)butyl, 3-(2-methyl-propoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methyl-propoxy)butyl or 4-(1,1-dimethylethoxy)butyl, preferably $CH_2—OCH_3$, $CH_2—OC_2H_5$, 2-methoxyethyl or 2-ethoxyethyl;

$C_3–C_4$-alkenyl: unsaturated, straight-chain or branched hydro-carbon radicals having 3 to 4 carbon atoms and a double bond in any position, preferably in the 1 position, for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2–C_4$-alkenyl and the alkenyl moieties of $C_2–C_4$-alkenyloxy: ethenyl or $C_3–C_4$-alkenyl (as mentioned above);

$C_2–C_4$-haloalkenyl and the haloalkenyl moieties of $C_2–C_4$-haloalkenyloxy: unsaturated, straight-chain or branched hydrocarbon radicals having 2 to 4 carbon atoms and a double bond in any position (as mentioned above), where the hydrogen atoms in these groups may be partially or fully replaced by halogen atoms as mentioned above, in particular by fluorine, chlorine and bromine;

$C_3–C_4$-alkynyl: straight-chain or branched hydrocarbon radicals having 3 to 4 carbon atoms and a triple bond in any position, preferably in the 1 position, for example ethynyl, 1-propynyl, 2-propynyl, 1-butynyl, 2-butynyl, 3-butynyl and 1-methyl-2-propynyl;

$C_2–C_4$-alkynyl and the alkynyl moieties of $C_2–C_4$-alkynyloxy: ethynyl or $C_3–C_4$-alkynyl (as mentioned above);

$C_2–C_4$-haloalkynyl and the haloalkynyl moieties of $C_2–C_4$-haloalkynyloxy: unsaturated, straight-chain or branched hydrocarbon radicals having 2 to 4 carbon atoms and a triple bond in any position (as mentioned above), where the hydrogen atoms in these groups may be partially or fully replaced by halogen atoms as mentioned above, in particular by fluorine, chlorine and bromine;

$C_3–C_8$-cycloalkyl: cyclopropyl, cyclobutyl, cyclopentyl, cyclohexyl, cycloheptyl or cyclooctyl;

$C_3–C_9$-cycloalkyl containing a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

$C_5–C_8$-cycloalkenyl: cyclopenten-2-yl, cyclohexen-2-yl, cyclohepten-2-yl, cycloocten-2-yl, cyclopenten-1-yl, cyclohexen-3-yl, cyclohepten-3-yl, cyclooten-3-yl or cycloocten-4-yl;

cyano-$C_1–C_4$-alkyl: cyanomethyl, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-cyanomethyleth-1-yl, 1-cyanomethyl-1-methyleth-1-yl or 1-cyanomethylprop-1-yl, preferably cyanomethyl or 2-cyanoethyl;

tris($C_1–C_4$-alkyl)silyl and the tris($c_1–C_4$-alkyl) silylresidue in tris($C_1–C_4$-alkyl)silyloxy: a radical of the formula $R^a{}_3Si$, where $R^a$ is $C_2–C_4$-alkyl and may be the same or different, e.g. trimethylsilyl, triethylsilyl, dimethylethylsilyl, dimethylisopropylsilyl, dimethyl-n-butylsilyl or dimethyl-tert-butylsilyl;

The 5 or 6-membered heterocycles which have 1, 2, or 3 heteroatoms being selected from O, S and N can be saturated, partially or fully unsaturated or aromatic. Saturated 5- or 6-membered heterocycles may also contain a carbonyl or thiocarbonyl ring member.

Examples of saturated heterocycles containing a carbonyl or thiocarbonyl ring member are: tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyran-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl.

Examples of partially unsaturated heterocycles are: dihydrofuran-2-yl, 1,2-oxazolin-3-yl, 1,2-oxazolin-5-yl, 1,3-oxazolin-2-yl.

Examples of aromatic heterocycles are furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-triazin-3-yl, in particular pyridyl, pyrimidyl, furanyl and thienyl.

With respect to their intended use as fungicides, preference is given to thiazolo[4,5-b]pyridines of the formula I, wherein at least one of the radicals $R^1$ to $R^3$ and particularly preferred $R^2$ is different from hydrogen. Particular preference is given to those thiazolo[4,5-b]pyridines of the formula I wherein the radicals $R^1$ to $R^3$ are as defined below, in each case on their own or in combination:

$R^1$ hydrogen or $C_1$–$C_4$-alkyl, especially hydrogen, or methyl;

$R^2$ hydrogen, halogen, $C_1$–$C_4$-alkyl, $C_1$–$C_4$-haloalkyl, especially hydrogen, chlorine, bromine, methyl or trifluoromethyl;

$R^3$ hydrogen;

In a preferred embodiment of the invention the variable A in formula I is selected from methylene, 1,2-ethylene, 1,1-ethylene or 1,3-propylene.

In a particularly preferred embodiment of the invention R in formula I is phenyl, phenoxy, a 5 or a 6 membered heterocycle, which has 1, 2, or 3, preferably 1 or 2 heteroatoms being selected from O, S and N, and which may be saturated, unsaturated or aromatic. Phenyl, phenoxy and the heterocycle, independently of each other, may be unsubstituted or substituted as defined above. Preferred substituents on phenyl, phenoxy and heterocyclyl are: F, Cl, methyl, difluoromethyl, trifluoromethyl, methoxy, difluoromethoxy, trifluoromethoxy, or phenyl which is unsubstituted or substituted as defined above. In this embodiment, preference is given to thiazolo[4,5-b]pyridines I, where R is phenyl, phenoxy, furyl, thiophenyl, or pyridyl, each of which may be unsubstituted or substituted as defined above.

In another preferred embodiment of the invention R is selected from cyano, $C_1$–$C_4$-alkoxy, cyano-$C_1$–$C_4$-alkyl, $C_1$–$C_4$-alkoxy-$C_1$–$C_4$-alkyl, tris($C_1$–$C_4$-alkyl)silyl, tris ($C_1$–$C_4$-alkyl)silyloxy, COR$^4$, COOR$^5$, CONR$^6$R$^7$ or S(O)$_k$R$^8$, wherein the radicals $R^4$ to $R^8$ and the integer k are defined as above. The integer k is preferably 2. Preferably $R^4$ to $R^8$ have the meanings listed below:

$R^4$ is $C_1$–$C_4$-alkyl and phenyl which may carry 1, 2, 3 or 4 substituents on the phenyl ring being selected, independently of one another, from halogen and $C_1$–$C_4$-alkyl;

$R^5$ is $C_1$–$C_6$-alkyl, $C_1$–$C_4$-alkoxy-$C_1$–$C_4$-alkyl, phenyl, and phenyl-$C_1$–$C_4$-alkyl, wherein phenyl and phenyl-$C_1$–$C_4$-alkyl may carry 1 or 2 substituents on the phenyl ring which are selected, independently of one another, from halogen, nitro, cyano, $C_1$–$C_4$-alkyl, $C_1$–$C_4$-alkoxy, OCHF$_2$ and CF$_3$;

$R^6$,$R^7$ independently from one another are hydrogen, $C_1$–$C_6$-alkyl, or may together with the nitrogen atom form a morpholinyl, piperidinyl, piperazinyl or pyrrolidinyl radical;

$R^8$ is phenyl, which may carry 1 or 2 substituents being selected, independently of one another, from halogen, $C_1$–$C_4$-alkyl and CF$_3$.

Preference is given to thiazolo[4,5-b]pyridines of the formula I, where the variable n is 1 or 2.

Representative examples of thiazolo[4,5-b]pyridines of the formula I, wherein $R^3$ is hydrogen are listed in table 1.

TABLE 1 thiazolo[4,5-b]pyridines I.1 to I.311.

| Ex. | $R^1$ | $R^2$ | n | A-R | HPLC [t in s] | MS[1] [m/z] | MM[2] [D] |
|---|---|---|---|---|---|---|---|
| 1. | H | Cl | 0 | n-$C_4H_9$ | | | |
| 2. | H | Cl | 0 | $(CH_2)_2CH=CH_2$ | | | |
| 3. | H | Cl | 0 | $(CH_2)_2Ph$ | | | |
| 4. | H | Cl | 0 | $(CH_2)_2(4\text{-ClPh})$ | | | |
| 5. | H | Cl | 0 | i-$C_3H_7$ | | | |
| 6. | H | Cl | 0 | $CH_2OCH_3$ | | | |
| 7. | H | Cl | 0 | n-$C_3H_7$ | | | |
| 8. | H | Cl | 0 | $CH_2(c\text{-}C_3H_5)$ | | | |
| 9. | H | Cl | 0 | c-$C_4H_8$ | | | |
| 10. | H | Cl | 0 | c-$C_5H_{10}$ | | | |
| 11. | H | Cl | 0 | $C_2H_5$ | | | |
| 12. | H | Cl | 0 | $CH_2CH=CH_2$ | | | |
| 13. | H | Cl | 0 | $(CH_2)_3COOC_2H_5$ | | | |
| 14. | H | Cl | 0 | $CH_2(4\text{-ClPh})$ | | | |
| 15. | H | Cl | 0 | $CH_2CH_2OPh$ | | | |
| 16. | H | Cl | 0 | $CH_2(4\text{-}(CF_3)Ph)$ | | | |
| 17. | H | Cl | 0 | $CH_2Ph$ | | | |
| 18. | H | Cl | 0 | $CH_2COOCH_3$ | | | |
| 19. | H | Cl | 0 | $CH_2CONH_2$ | | | |
| 20. | H | Cl | 0 | n-$C_7H_{15}$ | | | |
| 21. | H | Cl | 0 | $(CH_2)_5CN$ | | | |
| 22. | H | Cl | 0 | $(CH_2)_3Cl$ | | | |
| 23. | H | Br | 0 | $C_2H_5$ | | | |
| 24. | H | Br | 0 | n-$C_4H_9$ | | | |
| 25. | H | Br | 0 | $CH_2$-i-$C_3H_7$ | | | |
| 26. | H | Br | 0 | $CH_2CH_2$-t-$C_4H_9$ | | | |
| 27. | H | Br | 0 | $CH_2CH_2$-i-$C_3H_7$ | | | |
| 28. | H | Br | 0 | i-$C_3H_7$ | | | |
| 29. | H | Br | 0 | $CH_2$-c-$C_3H_5$ | | | |
| 30. | H | Br | 0 | $CH_2$-c-$C_4H_7$ | | | |
| 31. | H | Br | 0 | $CH_2$-c-$C_6H_{11}$ | | | |

TABLE 1-continued thiazolo[4,5-b]pyridines I.1 to I.311.

| Ex. | $R^1$ | $R^2$ | n | A-R | HPLC [t in s] | MS[1] [m/z] | MM[2] [D] |
|---|---|---|---|---|---|---|---|
| 32. | H | Br | 0 | $CH_2[4-(CF_3)Ph]$ | | | |
| 33. | H | Br | 0 | $CH_2Ph$ | | | |
| 34. | H | Br | 0 | $c-C_5H_9$ | | | |
| 35. | H | Br | 0 | $c-C_6H_{11}$ | | | |
| 36. | H | Br | 0 | $c-C_7H_{13}$ | | | |
| 37. | H | Br | 0 | $c-C_8H_{15}$ | | | |
| 38. | H | Br | 0 | 2-cyclohexenyl | | | |
| 39. | H | Br | 0 | $CH_2CH=CH_2$ | | | |
| 40. | H | Br | 0 | $CH_2C(CH_3)=CH_2$ | | | |
| 41. | H | Br | 0 | $CH_2C\equiv CH$ | | | |
| 42. | H | Br | 0 | $CH_2Si(CH_3)_3$ | | | |
| 43. | H | Br | 0 | $CH_2O-n-C_8H_{17}$ | | | |
| 44. | H | Br | 0 | $CH_2SCH_3$ | | | |
| 45. | H | Br | 0 | $CH_2O(4-ClPh)$ | | | |
| 46. | H | Br | 0 | $CH_2SO_2Ph$ | | | |
| 47. | H | Br | 0 | $CH_2CH_2CN$ | | | |
| 48. | H | Br | 0 | $(CH_2)_3COOC_2H_5$ | | | |
| 49. | H | Br | 0 | $CH_2COPh$ | | | |
| 50. | H | Br | 0 | $CH_2CONH_2$ | | | |
| 51. | H | Br | 0 | $CH_2CH_2OPh$ | | | |
| 52. | H | Br | 0 | $(CH_2)_3$-(4-Pyridyl) | | | |
| 53. | H | $CH_3$ | 0 | $n-C_4H_9$ | | | |
| 54. | H | $CH_3$ | 0 | $CH_2CH_2-t-C_4H_9$ | | | |
| 55. | H | $CH_3$ | 0 | $CH_2CH_2-i-C_3H_7$ | | | |
| 56. | H | $CH_3$ | 0 | $i-C_3H_7$ | | | |
| 57. | H | $CH_3$ | 0 | $CH_2Si(CH_3)_2(t-C_4H_9)$ | | | |
| 58. | H | $CH_3$ | 0 | $CH_2-c-C_3H_5$ | | | |
| 59. | H | $CH_3$ | 0 | $c-C_6H_{12}$ | | | |
| 60. | H | $CH_3$ | 0 | $c-C_5H_9$ | | | |
| 61. | H | $CH_3$ | 0 | $CH_2Ph$ | | | |
| 62. | H | $CH_3$ | 0 | $CH(CH_3)Ph$ | | | |
| 63. | H | $CH_3$ | 0 | $(CH_2)_3$-(4-Pyridyl) | | | |
| 64. | H | $CH_3$ | 0 | $CH_2CH_2OPh$ | | | |
| 65. | H | $CH_3$ | 0 | $CH_2O(4-ClPh)$ | | | |
| 66. | H | $CH_3$ | 0 | $CH_2COCH_3$ | | | |
| 67. | H | $CH_3$ | 0 | $CH_2CO-t-C_4H_9$ | | | |
| 68. | H | $CH_3$ | 0 | $CH(CH_3)CONH_2$ | | | |
| 69. | H | $CH_3$ | 0 | $CH_2SO_2Ph$ | | | |
| 70. | H | H | 0 | $CH_2Ph$ | 3.115 | 259 | 258.37 |
| 71. | H | H | 0 | $CH_2-i-C_3H_7$ | 3.133 | 225.05 | 224.35 |
| 72. | H | H | 0 | $CH_2CH_2OPh$ | 3.139 | 289.05 | 288.39 |
| 73. | H | H | 0 | $2-(CH_3O-CH_2CH_2O)C_2H_4$ | 2.169 | 271.05 | 270.37 |
| 74. | H | H | 0 | $CH=CH_2$ | 2.785 | 209 | 208.31 |
| 75. | H | H | 0 | $n-C_4H_9$ | 3.182 | 225.05 | 224.35 |
| 76. | H | H | 0 | $CH_2[3-(CF_3)Ph]$ | 3.224 | 327 | 326.36 |
| 77. | H | H | 0 | $CH_2CF_3$ | 2.788 | 251.95 | 250.27 |
| 78. | H | H | 0 | $CH_2(3-ClPh)$ | 3.288 | 293.95 | 292.81 |
| 79. | H | H | 0 | $CH_2CH_2[4-(NO_2)Ph]$ | 2.929 | 318 | 317.39 |
| 80. | H | H | 0 | $CH_2[3-(OCF_3)Ph]$ | 3.287 | 344 | 342.36 |
| 81. | H | H | 0 | $CH_2[4-(OCF_3)Ph]$ | 3.322 | 303.05 | 302.42 |
| 82. | H | H | 0 | $CH_2C(CH_3)=CH_2$ | 2.983 | 223 | 222.33 |
| 83. | H | H | 0 | $CH_2[3,5-(OCH_3)_2Ph]$ | 2.914 | 319.05 | 318.42 |
| 84. | $CH_3$ | Br | 0 | $CH_2Ph$ | 3.435 | 352 | 351.29 |
| 85. | $CH_3$ | Br | 0 | $CH_2-i-C_3H_7$ | 3.503 | 318.05 | 317.27 |
| 86. | $CH_3$ | Br | 0 | $2-(C_2H_5O)Ph$ | 3.510 | 382.05 | 381.32 |
| 87. | $CH_3$ | Br | 0 | $2-(CH_3O-CH_2CH_2O)C_2H_4$ | 2.708 | 364.05 | 363.3 |
| 88. | $CH_3$ | Br | 0 | $CH=CH_2$ | 3.175 | 302.95 | 301.23 |
| 89. | $CH_3$ | Br | 0 | $n-C_4H_9$ | 3.528 | 318 | 317.27 |
| 90. | $CH_3$ | Br | 0 | $CH_2[3-(CF_3)Ph]$ | 3.546 | 420.05 | 419.29 |
| 91. | $CH_3$ | Br | 0 | $CH_2CF_3$ | 3.106 | 344.95 | 343.19 |
| 92. | $CH_3$ | Br | 0 | $CH_2(3-ClPh)$ | 3.583 | 386.95 | 385.73 |
| 93. | $CH_3$ | Br | 0 | $CH_2CH_2[4-(NO_2)Ph]$ | 3.289 | 410.95 | 410.31 |
| 94. | $CH_3$ | Br | 0 | $CH_2[3-(OCF_3)Ph]$ | 3.597 | 436.95 | 435.29 |
| 95. | $CH_3$ | Br | 0 | $CH_2[4-(OCF_3)Ph]$ | 3.646 | 396.05 | 395.34 |
| 96. | $CH_3$ | Br | 0 | $CH_2C(CH_3)=CH_2$ | 3.338 | 316.95 | 315.26 |
| 97. | $CH_3$ | Br | 0 | $CH_2[3,5-(OCH_3)_2Ph]$ | 3.267 | 412.05 | 411.34 |
| 98. | $CH_3$ | Br | 0 | $c-C_5H_9$ | 3.55 | 330.05 | 329.28 |
| 99. | $CH_3$ | Br | 0 | 2-thiophenyl | 3.086 | 344.05 | 343.29 |
| 100. | $CH_3$ | Br | 0 | $CH=C(CH_3)_2$ | 3.186 | 316.05 | 315.26 |
| 101. | $CH_3$ | Br | 0 | $CH_2$-tetrahydropyran-3-yl | 3.495 | 376.05 | 375.37 |
| 102. | $CH_3$ | Br | 0 | $CH_2CH_2CH=CH_2$ | 3.394 | 316.05 | 315.26 |
| 103. | $CH_3$ | Br | 0 | $n-C_3H_7$ | 3.359 | 304.05 | 303.24 |
| 104. | $CH_3$ | Br | 0 | $CH_2-t-C_4H_9$ | 3.661 | 332.05 | 331.3 |

TABLE 1-continued thiazolo[4,5-b]pyridines I.1 to I.311.

| Ex. | $R^1$ | $R^2$ | n | A-R | HPLC [t in s] | MS[1] [m/z] | MM[2] [D] |
|---|---|---|---|---|---|---|---|
| 105. | $CH_3$ | Br | 0 | $C(CH_3)=CH_2$ | 3.208 | 302.95 | 301.23 |
| 106. | $CH_3$ | Br | 0 | c-$C_4H_7$ | 3.376 | 316.05 | 315.26 |
| 107. | $CH_3$ | Br | 0 | $CH_2[2,6-(F)_2Ph]$ | 3.420 | 388.95 | 387.27 |
| 108. | $CH_3$ | Br | 0 | 3-thiophenyl | 3.038 | 344.5 | 343.29 |
| 109. | $CH_3$ | Br | 0 | $CH_2CHF_2$ | 3.113 | 326.8 | 325.2 |
| 110. | $CH_3$ | Br | 0 | $CH_2$-c-$C_3H_5$ | 3.383 | 316.05 | 315.26 |
| 111. | $CH_3$ | Br | 0 | $CH_2[2-(Ph)Ph]$ | 3.812 | 428.05 | 427.39 |
| 112. | $CH_3$ | Br | 0 | $CH_2[3,4-(Cl)_2Ph]$ | 3.870 | 421.05 | 420.18 |
| 113. | $CH_3$ | Br | 0 | $CH_2$-[3-$CH_3$-1,1-$(Cl)_2$-cyclopropan-2-yl] | 3.076 | 360.05 | 359.31 |
| 114. | $CH_3$ | Br | 0 | $CH_2$-tetrahydrothio-pyran-3-yl | 3.673 | 399.95 | 398.17 |
| 115. | $CH_3$ | Br | 0 | $CH_2[2,5-(Cl)_2Ph]$ | 3.839 | 420.95 | 420.18 |
| 116. | $CH_3$ | Br | 0 | $CH_2(2-FPh)$ | 3.476 | 370 | 369.28 |
| 117. | $CH_3$ | Br | 0 | $CH_2(4-FPh)$ | 3.464 | 370.05 | 369.28 |
| 118. | $CH_3$ | Br | 0 | $CH_2[4-(NO_2)Ph]$ | 3.215 | 397 | 396.29 |
| 119. | $CH_3$ | Br | 0 | $CH_3$ | 2.863 | 276 | 275.19 |
| 120. | H | $CH_3$ | 0 | $CH_2Ph$ | 3.000 | 273.05 | 272.39 |
| 121. | H | $CH_3$ | 0 | $CH_2$-i-$C_3H_7$ | 2.904 | 239.05 | 238.38 |
| 122. | H | $CH_3$ | 0 | 2-$(C_2H_5O)Ph$ | 2.965 | 303.1 | 302.42 |
| 123. | H | $CH_3$ | 0 | 2-$(CH_3O-CH_2CH_2O)C_2H_4$ | 1.877 | 285.05 | 284.4 |
| 124. | H | $CH_3$ | 0 | $CH=CH_2$ | 2.427 | 223.05 | 222.33 |
| 125. | H | $CH_3$ | 0 | n-$C_4H_9$ | 2.934 | 239.15 | 238.38 |
| 126. | H | $CH_3$ | 0 | $CH_2[3-(CF_3)Ph]$ | 3.095 | 341.05 | 340.39 |
| 127. | H | $CH_3$ | 0 | $CH_2CF_3$ | 2.584 | 265.05 | 264.29 |
| 128. | H | $CH_3$ | 0 | $CH_2(3-ClPh)$ | 3.103 | 307.05 | 306.84 |
| 129. | H | $CH_3$ | 0 | $CH_2CH_2[4-NO_2Ph]$ | 2.794 | 332.05 | 331.42 |
| 130. | H | $CH_3$ | 0 | $CH_2[3-(OCF_3)Ph]$ | 3.157 | 357.05 | 356.39 |
| 131. | H | $CH_3$ | 0 | $CH_2[4-(OCF_3)Ph]$ | 3.151 | 317.15 | 316.45 |
| 132. | H | $CH_3$ | 0 | $CH_2C(CH_3)=CH_2$ | 2.711 | 237.1 | 236.36 |
| 133. | H | $CH_3$ | 0 | [2-$CH_3$-5-$(NO_2)$furyl] | 2.373 | 308.05 | 307.35 |
| 134. | H | $CH_3$ | 0 | $CH_2[3,5-(OCH_3)_2Ph]$ | 2.719 | 333.1 | 332.45 |
| 135. | H | $CH_3$ | 0 | c-$C_5H_9$ | 2.992 | 251.15 | 250.39 |
| 136. | H | $CH_3$ | 0 | 4-$CH_3$-c-$C_6H_{10}$ | 3.365 | 279.15 | 278 |
| 137. | H | $CH_3$ | 0 | $CH=C(CH_3)_2$ | 2.736 | 237.05 | 236.36 |
| 138. | H | $CH_3$ | 0 | $CH_2$-tetrahydropy-ran-3-yl | 2.936 | 297.05 | 296.48 |
| 139. | H | $CH_3$ | 0 | $CH_2CH_2CH=CH_2$ | 2.759 | 237.05 | 236.36 |
| 140. | H | $CH_3$ | 0 | n-$C_3H_7$ | 2.66 | 225.05 | 224.35 |
| 141. | H | $CH_3$ | 0 | $CH_2$-t-$C_4H_9$ | 3.196 | 253.15 | 252.4 |
| 142. | H | $CH_3$ | 0 | $C(CH_3)=CH_2$ | 2.443 | 223.05 | 222.33 |
| 143. | H | $CH_3$ | 0 | c-$C_4H_7$ | 2.726 | 237.1 | 236.36 |
| 144. | H | $CH_3$ | 0 | $CH_2[2,6-(F)_2Ph]$ | 2.905 | 309.05 | 308.37 |
| 145. | H | $CH_3$ | 0 | $CH_2CHF_2$ | 2.321 | 247.05 | 246.3 |
| 146. | H | $CH_3$ | 0 | $CH_2$-c-$C_3H_5$ | 2.707 | 237.1 | 236.36 |
| 147. | H | $CH_3$ | 0 | $CH_2[2-(Ph)Ph]$ | 3.347 | 349.15 | 348.49 |
| 148. | H | $CH_3$ | 0 | $CH_2[3,4-(Cl)_2Ph]$ | 3.276 | 342.05 | 341.28 |
| 149. | H | $CH_3$ | 0 | $CH_2$-[3-$CH_3$-1,1-$(Cl)_2$-cyclopropan-2-yl] | 2.36 | 281.15 | 280.41 |
| 150. | H | $CH_3$ | 0 | $CH_2$-tetrahydrothio-pyran-3-yl | 3.205 | 320.05 | 319.28 |
| 151. | H | $CH_3$ | 0 | $CH_2[2,5-(Cl)_2Ph]$ | 3.363 | 342.05 | 341.28 |
| 152. | H | $CH_3$ | 0 | $CH_2[2-(CF_3)Ph]$ | 3.21 | 341.05 | 340.39 |
| 153. | H | $CH_3$ | 0 | $CH_2(2-FPh)$ | 2.956 | 291.05 | 290.38 |
| 154. | H | $CH_3$ | 0 | $CH_2(4-FPh)$ | 2.936 | 291.05 | 290.38 |
| 155. | H | $CH_3$ | 0 | $CH_2(4-(NO_2)Ph)$ | 2.699 | 318.1 | 317.39 |
| 156. | H | $CH_3$ | 0 | $CH_3$ | 1.798 | 197.05 | 196.29 |
| 157. | H | Cl | 1 | n-$C_4H_9$ | | | |
| 158. | H | Cl | 1 | $(CH_2)_2CH=CH_2$ | | | |
| 159. | H | Cl | 1 | $(CH_2)_2Ph$ | | | |
| 160. | H | Cl | 1 | $(CH_2)_2(4-ClPh)$ | | | |
| 161. | H | Cl | 1 | c-$C_5H_9$ | | | |
| 162. | H | Cl | 1 | n-$C_3H_7$ | | | |
| 163. | H | Cl | 1 | $CH_2CH=CH_2$ | | | |
| 164. | H | Cl | 1 | $C_2H_5$ | | | |
| 165. | H | Cl | 1 | $CH_2$-c-$C_3H_7$ | | | |
| 166. | H | Cl | 1 | $(CH_2)_3COOC_2H_5$ | | | |
| 167. | H | Cl | 1 | $CH_2CH_2OPh$ | | | |
| 168. | H | Cl | 1 | $CH_2O(4-ClPh)$ | | | |
| 169. | H | Cl | 1 | $CH_2Ph$ | | | |
| 170. | H | Br | 1 | $C_2H_5$ | | | |
| 171. | H | Br | 1 | $nC_4H_9$ | | | |
| 172. | H | Br | 1 | $CH_2$-i-$C_3H_7$ | | | |
| 173. | H | Br | 1 | $CH_2CH_2$-t-Bu | | | |

TABLE 1-continued thiazolo[4,5-b]pyridines I.1 to I.311.

| Ex. | $R^1$ | $R^2$ | n | A-R | HPLC [t in s] | MS[1] [m/z] | MM[2] [D] |
|---|---|---|---|---|---|---|---|
| 174. | H | Br | 1 | $CH_2CH_2$-i-Pr | | | |
| 175. | H | Br | 1 | i-$C_3H_7$ | | | |
| 176. | H | Br | 1 | $CH_2$-c-$C_3H_5$ | | | |
| 177. | H | Br | 1 | $CH2$-c-$C_4$—$H_7$ | | | |
| 178. | H | Br | 1 | $CH_2$-c-$C_6H_{11}$ | | | |
| 179. | H | Br | 1 | $CH_2$(4-($CF_3$)Ph) | | | |
| 180. | H | Br | 1 | $CH_2$Ph | | | |
| 181. | H | Br | 1 | $CH_2C=CH_2(CH_3)$ | | | |
| 182. | H | Br | 1 | $CH_2CH=(CH_3)_2$ | | | |
| 183. | H | Br | 1 | $CH_2Si(CH_3)_3$ | | | |
| 184. | H | Br | 1 | $CH_2OC_8H_{17}$ | | | |
| 185. | H | Br | 1 | $CH_2CH_2CN$ | | | |
| 186. | H | Br | 1 | $(CH_2)_3COOC_2H_5$ | | | |
| 187. | H | Br | 1 | $CH_3CH_2OPh$ | | | |
| 188. | H | Br | 1 | $(CH_2)_3$-4-Pyridyl | | | |
| 189. | H | Br | 1 | n-$C_4H_9$ | | | |
| 190. | H | Br | 1 | $CH_2CH_2$-t-Bu | | | |
| 191. | H | Br | 1 | $CH_2CH_2$-i-$C_3H_7$ | | | |
| 192. | H | Br | 1 | $CH_2$-c-$C_3H_5$ | | | |
| 193. | H | Br | 1 | $CH_2$-c-$C_6H_{11}$ | | | |
| 194. | H | Br | 1 | $CH_2$Ph | | | |
| 195. | H | Br | 1 | $CH_2CH_2OPh$ | | | |
| 196. | H | H | 1 | $CH_2$Ph | 2.24 | 275 | 274.37 |
| 197. | H | H | 1 | $CH_2$-i-$C_3H_7$ | 2.105 | 241.05 | 240.35 |
| 198. | H | H | 1 | 2-($C_2H_5O$)Ph ?? | 2.289 | 305.05 | 304.39 |
| 199. | H | H | 1 | 2-($CH_3O$—$CH_2CH_2O$)$C_2H_4$ | 1.477 | 287.15 | 286.37 |
| 200. | H | H | 1 | n-$C_4H_9$ | 2.134 | 241.05 | 240.35 |
| 201. | H | H | 1 | $CH_2$[3-($CF_3$)Ph] | 2.522 | 343 | 342.36 |
| 202. | H | H | 1 | $CH_2CF_3$ | 1.89 | 268 | 266.27 |
| 203. | H | H | 1 | $CH_2$(3-ClPh) | 2.522 | 309.85 | 308.81 |
| 204. | H | H | 1 | $CH_2CH_2$[4-($NO_2$)Ph] | 2.174 | 334 | 333.39 |
| 205. | H | H | 1 | $CH_2$[3-($OCF_3$)Ph] | 2.596 | 359 | 358.36 |
| 206. | H | H | 1 | $CH_2$[4-($OCF_3$)Ph] | 2.526 | 319 | 318.42 |
| 207. | H | H | 1 | $CH_2$[3,5-($OCH_3$)$_2$Ph] | 2.102 | 335.05 | 334.42 |
| 208. | H | $CH_3$ | 1 | c-$C_5H_9$ | 3.556 | 330.05 | 329.28 |
| 209. | H | $CH_3$ | 1 | 4-$CH_3$-c-$C_6H_{10}$ | 3.894 | 358.1 | 357 |
| 210. | H | $CH_3$ | 1 | $CH=C(CH_3)_2$ | 3.186 | 315.05 | 315.26 |
| 211. | H | $CH_3$ | 1 | $CH_2CH_2CH=CH_2$ | 3.394 | 316.05 | 315.26 |
| 212. | H | $CH_3$ | 1 | n-$C_3H_7$ | 3.359 | 304.05 | 303.24 |
| 213. | H | $CH_3$ | 1 | $CH_2$-t-$C_4H_9$ | 3.661 | 332.05 | 331.3 |
| 214. | H | $CH_3$ | 1 | $C(CH_3)=CH_2$ | 3.208 | 302.95 | 301.23 |
| 215. | H | $CH_3$ | 1 | c-$C_4H_7$ | 3.376 | 316.05 | 315.26 |
| 216. | H | $CH_3$ | 1 | $CH_2$[2,6-(F)$_2$—Ph] | 3.463 | 388.95 | 387.27 |
| 217. | H | $CH_3$ | 1 | $CH_2CHF_2$ | 3.011 | 326.95 | 325.2 |
| 218. | H | $CH_3$ | 1 | $CH_2$-c-$C_3H_5$ | 3.338 | 316.05 | 315.26 |
| 219. | H | $CH_3$ | 1 | $CH_2$[2-(Ph)Ph] | 3.812 | 428.05 | 427.39 |
| 220. | H | $CH_3$ | 1 | $CH_2$[3,4-(Cl)$_2$Ph] | 3.73 | 421.95 | 420.18 |
| 221. | H | $CH_3$ | 1 | $CH_2$[2,5-(Cl)$_2$Ph] | 3.839 | 422.05 | 420.18 |
| 222. | H | $CH_3$ | 1 | $CH_2$(2-FPh) | 3.527 | 370 | 369.28 |
| 223. | H | $CH_3$ | 1 | $CH_2$(4-FPh) | 3.464 | 370.05 | 369.28 |
| 224. | H | $CH_3$ | 1 | $CH_2$[4-($NO_2$)Ph] | 3.215 | 397 | 396.29 |
| 225. | H | $CH_3$ | 1 | $CH_3$ | 2.863 | 277 | 275 |
| 226. | H | Cl | 2 | $CH_3$ | | | |
| 227. | H | Cl | 2 | $(CH_2)_2CH=CH_2$ | | | |
| 228. | H | Cl | 2 | n-$C_4H_9$ | | | |
| 229. | H | Cl | 2 | $(CH_2)_2$(4-ClPh) | | | |
| 230. | H | Cl | 2 | $(CH_2)_2$Ph | | | |
| 231. | H | Cl | 2 | i-$C_3H_7$ | | | |
| 232. | H | Cl | 2 | c-$C_5H_{10}$ | | | |
| 233. | H | Cl | 2 | n-$C_3H_7$ | | | |
| 234. | H | Cl | 2 | $C_2H_5$ | | | |
| 235. | H | Cl | 2 | $CH_2CH=CH_2$ | | | |
| 236. | H | Cl | 2 | $CH_2CH_2OPh$ | | | |
| 237. | H | Cl | 2 | $CH_2$[4-($CF_3$)Ph] | | | |
| 238. | H | Cl | 2 | $CH_2$Ph | | | |
| 239. | H | Br | 2 | $C_2H_5$ | | | |
| 240. | H | Br | 2 | n-$C_3H_7$ | | | |
| 241. | H | Br | 2 | n-$C_4H_9$ | | | |
| 242. | H | Br | 2 | $CH_2$-i-$C_3H_7$ | | | |
| 243. | H | Br | 2 | $CH_2CH_2$-t-$C_4H_9$ | | | |
| 244. | H | Br | 2 | $CH_2CH_2$-i-$C_3H_7$ | | | |
| 245. | H | Br | 2 | i-$C_3H_7$ | | | |
| 246. | H | Br | 2 | $CH_2$-c-$C_3H_5$ | | | |
| 247. | H | Br | 2 | $CH_2$-c-$C_4H_7$ | | | |

TABLE 1-continued thiazolo[4,5-b]pyridines I.1 to I.311.

| Ex. | $R^1$ | $R^2$ | n | A-R | HPLC [t in s] | MS[1] [m/z] | MM[2] [D] |
|---|---|---|---|---|---|---|---|
| 248. | H | Br | 2 | $CH_2$-c-$C_6H_{11}$ | | | |
| 249. | H | Br | 2 | $CH_2$[4-($CF_3$)Ph] | | | |
| 250. | H | Br | 2 | $CH_2$Ph | | | |
| 251. | H | Br | 2 | c-$C_5H_9$ | | | |
| 252. | H | Br | 2 | c-$C_6H_{11}$ | | | |
| 253. | H | Br | 2 | c-$C_7H_{13}$ | | | |
| 254. | H | Br | 2 | c-$C_8H_{15}$ | | | |
| 255. | H | Br | 2 | $CH_2CH=CH_2$ | | | |
| 256. | H | Br | 2 | $CH_2C=CH(CH_3)$ | | | |
| 257. | H | Br | 2 | $CH_2SCH_3$ | | | |
| 258. | H | Br | 2 | $(CH_2)_3COOC_2H_5$ | | | |
| 259. | H | Br | 2 | $CH_2CH_2OPh$ | | | |
| 260. | H | Br | 2 | $CH_3$ | | | |
| 261. | H | $CF_3$ | 2 | $CH_2CH_2OSi(CH_3)_2$t-$C_4H_9$ | | | |
| 262. | H | Br | 2 | $CH_2Si(CH_3)_2$t-$C_4H_9$ | | | |
| 263. | H | Br | 2 | $CH_2$-c-$C_4H_7$ | | | |
| 264. | H | $CH_3$ | 2 | n-$C_3H_7$ | | | |
| 265. | H | $CH_3$ | 2 | $CH_2$-i-$C_3H_7$ | | | |
| 266. | H | $CH_3$ | 2 | $CH(CH_3)$-n-$C_3H_7$ | | | |
| 267. | H | $CH_3$ | 2 | $CH(CH_3)$-n-$C_6H_{13}$ | | | |
| 268. | H | $CH_3$ | 2 | c-$C_6H_{11}$ | | | |
| 269. | H | $CH_3$ | 2 | c-$C_7H_{13}$ | | | |
| 270. | H | $CH_3$ | 2 | c-$C_8H_{15}$ | | | |
| 271. | H | $CH_3$ | 2 | $CH(CH_3)CONH_2$ | | | |
| 272. | H | $CH_3$ | 2 | $CH_2SO_2Ph$ | | | |
| 273. | H | $CH_3$ | 2 | $C_2H_5$ | | | |
| 274. | H | $CH_3$ | 2 | $CH_2CH_2$-i-$C_3H_7$ | | | |
| 275. | H | $CH_3$ | 2 | $CH_2$-c-$C_3H_7$ | | | |
| 276. | H | $CH_3$ | 2 | $CH_2Ph$ | | | |
| 277. | H | $CH_3$ | 2 | $CH_2CH_2OPh$ | | | |
| 278. | H | $CH_3$ | 2 | $(CH_2)_3$-4-Pyridyl | | | |
| 279. | H | H | 2 | $CH_2Ph$ | 2.225 | 291 | 290.36 |
| 280. | H | H | 2 | $CH_2$-i-$C_3H_7$ | 2.242 | 257.05 | 256.35 |
| 281. | H | H | 2 | 2-($C_2H_5O$)Ph | 2.388 | 321.05 | 320.39 |
| 282. | H | H | 2 | 2-($CH_3O$—$CH_2CH_2O$)$C_2H_4$ | 1.571 | 303.05 | 302.37 |
| 283. | H | H | 2 | n-$C_4H_9$ | 2.253 | 257.05 | 256.35 |
| 284. | H | H | 2 | $CH_2$[3-($CF_3$)Ph] | 2.629 | 359.05 | 358.36 |
| 285. | H | H | 2 | $CH_2CF_3$ | 2.109 | 283 | 282.26 |
| 286. | H | H | 2 | $CH_2$[3-ClPh] | 2.522 | 325.95 | 324.81 |
| 287. | H | H | 2 | $CH_2CH_2$[4-($NO_2$)Ph] | 2.235 | 350.05 | 349.39 |
| 288. | H | H | 2 | $CH_2$[3-($OCF_3$)Ph] | 2.708 | 375.05 | 374.36 |
| 289. | H | H | 2 | $CH_2$[4-($OCF_3$)Ph] | 2.532 | 335.05 | 334.42 |
| 290. | H | H | 2 | $CH_2$[3,5-($OCH_3$)$_2$Ph] | 2.213 | 351.05 | 350.42 |
| 291. | $CH_3$ | Br | 2 | $CH_2Ph$ | 2.729 | 384.9 | 383.29 |
| 292. | $CH_3$ | Br | 2 | $CH_2$-i-$C_3H_7$ | 2.771 | 350.9 | 349.47 |
| 293. | $CH_3$ | Br | 2 | 2-($C_2H_5O$)Ph | 2.797 | 414.9 | 413.31 |
| 294. | $CH_3$ | Br | 2 | 2-($CH_3O$—$CH_2CH_2O$)$C_2H_4$ | 2.293 | 395.9 | 395.3 |
| 295. | $CH_3$ | Br | 2 | n$C_4H_9$ | 2.772 | 350.9 | 349.27 |
| 296. | $CH_3$ | Br | 2 | $CH_2$[3-($CF_3$)Ph] | 3.001 | 452.9 | 451.29 |
| 297. | $CH_3$ | Br | 2 | $CH_2$[3-(Cl)Ph] | 2.951 | 418.8 | 417.73 |
| 298. | $CH_3$ | Br | 2 | $CH_2CH_2$[4-($NO_2$)Ph] | 2.653 | 442.9 | 442.13 |
| 299. | $CH_3$ | Br | 2 | $CH_2$[4-($OCF_3$)Ph] | 3.063 | 468.9 | 467.29 |
| 300. | $CH_3$ | Br | 2 | $CH_2$[3,5-($OCH_3$)$_2$Ph] | 2.770 | 444.9 | 443.34 |
| 301. | $CH_3$ | Br | 2 | $CH_2CF_3$ | 2.638 | 375.9 | 375.19 |
| 302. | H | $CH_3$ | 2 | $CH_2Ph$ | 2.545 | 305 | 304.39 |
| 303. | H | $CH_3$ | 2 | $CH_2$-i-$C_3H_7$ | 2.320 | 271 | 270.37 |
| 304. | H | $CH_3$ | 2 | 2-($C_2H_5O$)Ph | 2.382 | 335 | 334.42 |
| 305. | H | $CH_3$ | 2 | 2-($CH_3O$—$CH_2CH_2O$)$C_2H_4$ | 1.711 | 317 | 316.4 |
| 306. | H | $CH_3$ | 2 | n-$C_4H_9$ | 2.308 | 271 | 270.37 |
| 307. | H | $CH_3$ | 2 | $CH_2$[3-($CF_3$)Ph] | 2.798 | 373 | 372.39 |
| 308. | H | $CH_3$ | 2 | $CH_2CF_3$ | 2.166 | 296.9 | 296.29 |
| 309. | H | $CH_3$ | 2 | $CH_2$[3-(Cl)Ph] | 2.581 | 339.5 | 338.84 |
| 310. | H | $CH_3$ | 2 | $CH_2CH_2$[4-($NO_2$)Ph] | 2.293 | 364 | 363.42 |
| 311. | H | $CH_3$ | 2 | $CH_2$[4-($OCF_3$)Ph] | 2.574 | 349.9 | 348.39 |

[1]MS = mass spectrum
[2]MM = molar mass n-$C_mH_{2m+1}$: n-alkyl;
c-$C_mH_{2m-1}$: cycloalkyl;
i-$C_3H_7$: isopropyl;
t-$C_4H_9$: tert. butyl;
Ph: $C_6H_5$
2-FPh: 2-fluorophenyl;
4-FPh: 4 fluorophenyl;
3-ClPh: 3 chlorophenyl;
4-ClPh: 4 chlorophenyl;
2-($CF_3$)Ph: 2-(trifluoromethyl)phenyl;
3-($CF_3$)Ph: 3-(trifluoromethyl)phenyl;
4-($CF_3$)Ph: 4-(trifluoromethyl)phenyl;
3-($OCF_3$)Ph: 3-(trifluoromethoxy)phenyl;
4-($OCF_3$)Ph: 4-(trifluoromethoxy)phenyl;
4-($NO_2$)Ph: 4-nitrophenyl;
2-($C_2H_5O$)Ph: 2-ethoxyphenyl;
$CH_2$(4-FPh);
$CH_2$(2-FPh);
2-(Ph)Ph: o-biphenyl
3,5-($OCH_3$)$_2$Ph: 3,5-bis(methoxy)phenyl;
2,6-(F)$_2$Ph: 2,6-difluorophenyl;
3,4-(Cl)$_2$Ph: 3,4-dichlorophenyl;
2,5-(Cl)$_2$Ph: 2,5-dichlorophenyl;
2-$CH_3$-5-($NO_2$)furyl: 2-methyl-5-nitrofuryl;

The compounds of the formula I can be obtained according to the following reaction sequence shown in scheme 1:

In the formulae I, II, II and IV, the variables A, R, $R^1$, $R^2$, $R^3$ have the meanings as defined above. Hal denotes bromine or iodine. Halide means chloride, bromide or iodide.

In step a) 2-aminopyridines of the formula II are first halogenated to yield the 3-halo-2-amino pyridines of the formula III. Usually the bromination is carried out with bromine [cf.: A. Fuss, V. Koch, Synthesis 1990, 681–685; M. Tonga, J. Bupp, T. Tochimoto, J. Heterocycl. Chem. 1994, 31, 1641–1644] or N-bromosuccinimide (NBS) [cf.: J. Mouton, M. Schmitt, V. Collort, J. Bourguignon, Heterocycles 1997, 45, 897–910; R. Beugelmans, M. Chban, Bull. Soc. Chim. France, 1995, 132, 290–305]. The iodination can be accomplished by treatment of the 2-aminopyridines of the formula II with iodine or ICl [cf.: M. V. Jovanovic, Heterocycles 1994, 22, 1195–1210]. Particular preference is given to the bromination with bromine.

Advantageously the halogenation is carried out with at least one molar equivalent of halogen, preferably with 1.05 to 1.5 molar equivalents of halogen. The reaction is usually carried out in an inert organic solvent. Suitable solvents are carboxylic acids, preferably $C_2$–$C_5$-carboxylic acids, such as acetic acid, propionic acid, butyric acid and valeric acid, and cyclic or acyclic hydrocarbons, such as n-pentane, n-hexane, n-heptane, n-octane, petroleum ether, cyclohexane, or halogenated solvents, such as dichloromethane, trichloromethane. It is also possible to use mixtures of these solvents.

Scheme 1:

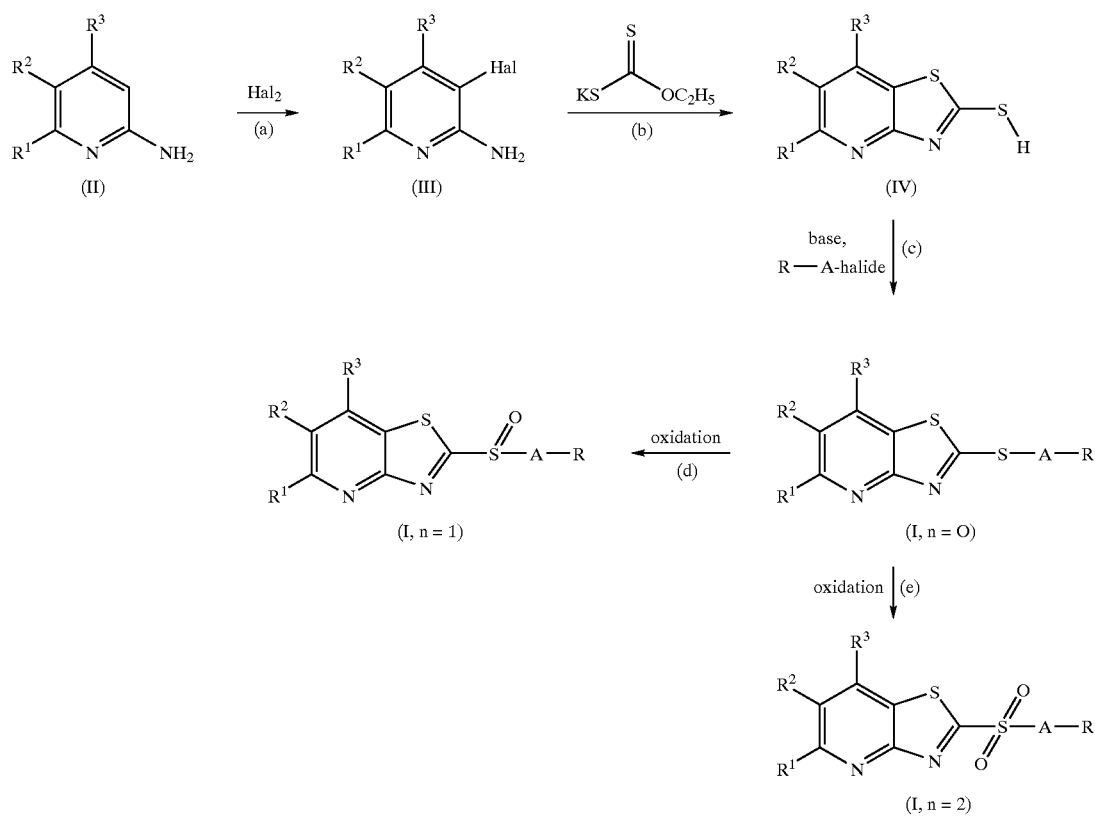

Hal = Br, I
halide = Cl, Br, I

The halogenation is usually carried out at a temperature from 0° C. to the boiling point of the solvent, preferably from 10° C. to 70° C.

The reaction mixtures are worked up in a customary fashion. The compounds III can be accompanied by side products resulting from the formation of regioisomers or double bromination. These side products can be removed by column chromatography or crystallisation.

Alternatively, as shown in scheme 2, it is possible to prepare the compound III according to the procedures described by L. Estel, F. Marsais, G. Queguiner, J. Org. Chem. 1988, 53, 2740–2744.

Scheme 2:

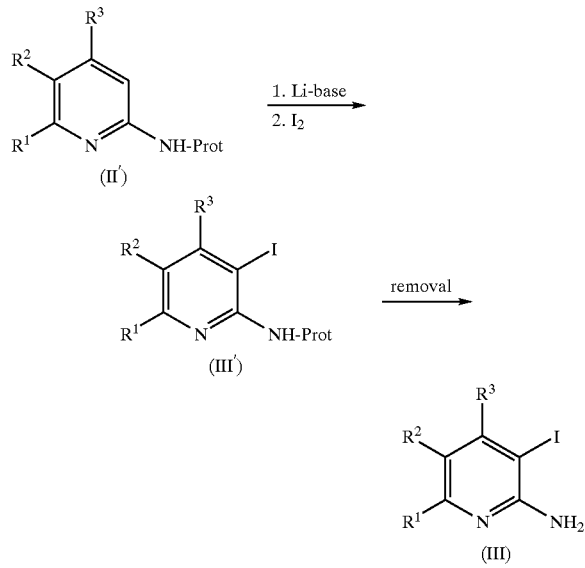

Initially the amino group is protected, for example by acylation. The pivaloyl group is a useful aminoprotecting group and can be introduced into II, e.g. by a method described by L. Estel, F. Marsais, G. Queguiner, J. Org. Chem. 1988, 53, 2740–2744. Then the corresponding 3-lithiopyridine is prepared by addition of a lithiumorganic compound, such as n-butyl- or t-butyllithium, phenyllithium or preferably in the presence of a secondary amine such as diisopropylamine, 2,2,6,6-tetramethylpiperidine or dicyclohexylamine or by addition of the corresponding lithium amides, such as lithium diisopropylamide, lithium 2,2,6,6-tetramethylpiperidide, lithium dicyclohexylamide or hexamethyldisilazane. In general more than one molar equivalent of lithiumorganic compound, preferably 1.1 to 5 molar equivalents, based on compound II, are required for the metallation. The resulting organolithium compounds are converted into the compound III by subsequent addition of iodine and cleavage of the protecting group. Usually a slight molar excess of iodine is used. The protecting group is removed for example by reacting III' with acids or bases, e.g. hydrochloric acid (Heterocycles, 1994, 39, S. 271) or lithium hydroxide (Tetrahedron Letters, 1997, 38, 4037).

The metallation and iodination are usually carried out at from −100° C. to 50° C., preferably at from −80° C. to 20° C. in an inert organic solvent. Suitable solvents are ethers, for example diethyl ether, methyl-tert.-butylether, diisopropylether, tetrahydrofuran, dioxane, 1,2-dimethoxyethane, alkanes, for example n-pentane, n-hexane, n-heptane, n-octane, petroleum ether and cy-=clohexane or mixture thereof.

The starting material, i.e. 2-aminopyridines of the formula II, required for preparing the compounds I are known from literature, or can be prepared by known methods [cf.: Pozharskii, Simonov, Doron'kin, Russ. Chem. Rev. 1978, 47, 1042–1060].

In step b) the compounds of formula III are treated with a potassium salt of a xanthogenic ester, preferably ethylxanthogenic acid potasssium salt, to yield the corresponding 2-thio thiazolo[4,5-b]pyridines of formula IV. The cyclization can be conducted similarly to the preparation of benzothiazoles from o-haloanilines, as described by N. C. Chaudhuri, Synth. Commun. 1996, 26, 3783–3790; N. Suzuki, Y. Tanaka, R. Dohmari, Chem. Pharm. Bull. 1079, 27, 1–11. Preferably compound III is treated with 1.5 to 5 molar equivalents of the potassium salt. The reaction is usually carried out in an polar solvent, e.g. water and/or alcohols, and/or aprotic polar solvents such as amides, e.g. N,N-dimethylformamide, N,N-dimethylacetamide, N-methylpyrrolidone or sulfoxides, e.g. dimethyl sulfoxide or mixture thereof. Preferably the reaction is conducted in N,N-dimethylformamide, N,N-dimethylacetamide, N-methylpyrrolidone or mixtures thereof. The use of aprotic polar solvents and additional water as cosolvent is possible (see EP-A 35219). In this case the amount of water is about 10 to 200% by weight based on the amount of organic solvent. The reaction is usually carried out at a temperature of from 25° C. to 250° C., preferably of from 60° C. to 210° C., especially above 180° C.

In step c) the group R is introduced to yield the thiazolo [4,5-b]pyridines of formula I, wherein n is 0. In order to obtain compounds I compounds IV can be reacted with an organic halide of the formula R—A-halide in the presence of a base. Halide means chloride, bromide or iodide. Bases which may be used are well known to those skilled in the art and are for example alkali carbonates, such as lithium carbonate, sodium carbonate, potassium carbonate, bicarbonates, such as magnesium carbonate, magnesium carbonate, alkali metal alkoxides, such as sodium methoxide, sodium ethoxide, potassium methoxide, potassium ethoxide, potassium tert-butoxide. Particular preference is given to sodium carbonate, potassium carbonate, sodium methoxide, potassium methoxide, sodium ethoxide and potassium ethoxide. In general a slight excess of the organic halide is used, preferably in the range of 1, 1 to 2 molar equivalents. The reaction is usually carried out in polar aprotic solvents, e.g. N,N-dimethylformamide, N,N-dimethylacetamide, N-methylpyrrolidone, ethers such as tetrahydrofuran, diethyl ether, methyl-tert.-butyl ether, sulfoxides, such as dimethyl sulfoxide or mixtures thereof, preferably in tetrahydrofuran, diethyl ether, methyl-tert.-butyl ether, N,N-dimethylformamide, N,N-dimethylacetamide, N-methylpyrrolidone or dimethylsulfoxide. The reaction is usually carried out at a temperature of about 0° C. to 200° C., preferably at a temperature of about 20° C. to 150° C.

Alternatively, the compounds I, wherein the radical —A—R represents an olefinically unsaturated group, can be prepared by reacting the compound IV with an aliphatic or cyclic aldehyde having an α-hydrogen in the presence of a Lewis acid, e.g. according to Mukaiama and Saigo, Chem. Lett. 479 (1973) or Akiyania, Bull. Chem. Soc. Jpn 50, 936 (1977).

In formula I, n can also be 1 or 2. The sulfide compound I with n=0 can be converted into to the sulfoxide compound I with n=1 by an approximately equimolar amount of hydrogen peroxide or by treatment with other oxidising agents such as tert.-butyl hydroperoxide or peracids, e.g. m-chloro perbenzoic acid, peracetic acid (step d)). The sulfoxide compound can be further oxidised to the sulfone compound I with n=2 by another mole of oxidising agent. The sulfide compound I (n=0) can be directly converted into the sulfone compound I (n=2) without isolation of the sulfoxide (step e)). Suitable solvents for step d) and e) are halogenated alkanes, such as dichloromethane, chloroform, tetrachloromethane or chlorobenzene, alkohols, such as methanol, ethanol, n-propanol, iso-propanol, n-butanol, amides as dimethylformamide, dimethylacetamide, cyclic or acyclic alkanes such as cyclohexane, hexane, pentane, heptane, petroleum ether. Preferred solvents are dichloromethane and chloroform. Usually the oxidation is carried out at about −80° C. to 100° C., preferably at about −20° C. to 50° C.

The compounds I are suitable as fungicides. They have outstanding activity against a broad spectrum of phytopathogenic fungi, in particular from the classes of the *Ascomycetes, Deuteromycetes, Phycomycetes* and *Basidiomycetes*. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Erysiphe graminis* (powdery mildew) on cereals,
*Fusarium* and *Verticillium* species on various plants,
*Helminthosporium* species on cereals,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria nodorum* on wheat,
*Uncinula necator* on grapevines,
*Ustilago* species on cereals and sugar cane, and
*Venturia* species (scab) on apples and pears.

Moreover, the compounds I are suitable for controlling harmful fungi such as *Paecilomyces variotii* in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 kg, preferably 0.01 to 0.05 kg, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which is comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill.

Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1, 2,2-tetrachloroe -thylthio)tetrahydrophthalimide, N-trichloromethylthiotetrahydrophthalimide, N-trichloromethylthiophthalimide, N-dichlorofluoromethylthio-N',N'-dimethyl-N-phenylsulfo-diamide, 5-ethoxy-3-trichloromethyl-1,2, 3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as methyl E-methoxyimino-[α-(o-tolyloxy)-o-tolyl]acetate, methyl E-2-{2-[6-(2-cyanophenoxy) pyrimidin-4-yloxy]-phenyl}-3-methoxyacrylate, methyl-E-methoxyimino-[α-(2-phenoxyphenyl)]-acetamide, methyl E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl]-aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichloro-phenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

SYNTHESIS EXAMPLES

Example 1

6-Chloro-2-[(3-allyl)thio]thiazolo[4,5-b]pyridine

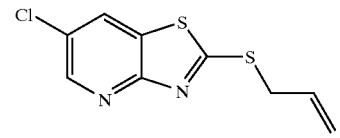

1.1 2-Amino-3-bromo-5-chloropyridine

A solution of 257 g (1.61 mol) of bromine in 380 ml of acetic acid was added dropwise over a period of one hour to a solution of 187 g (1.45 mol) of 2-amino-5-chloropyridine in 1.5 l of acetic acid. The reaction mixture was refluxed for 3 h and then allowed to cool to ambient temperature. 1.9 l of demineralized water were added and the mixture was concentrated in vacuo. The residue was partitioned between 4 l of ethyl acetate and 1.8 l of water. The mixture was basified with 3 l of a 10% by weight aqueous sodium hydroxide solution. The organic layer was separated and washed with brine (2×1.5 l), dried over magnesium sulfate, filtered and concentrated in vacuo. The residue was filtered, washed with hexane (2×100 ml) and dried in vacuo to give 192 g of 2-amino-3-bromo-5-chloropyridine. The mother liquor was concentrated in vacuo, filtered, washed with hexane and dried to give further 75 g of the same product.

1.2 6-Chloro-2-mercaptothiazolo[4,5-b]pyridine

A solution of 133 g (0.64 mol) of 2-amino-3-bromo-5-chloropyridine from Example 1.1 in 1.02 l of N-methylpyrrolidone was admixed with 205 g (1.28 mol) O-ethylxanthic acid potassium salt. The reaction mixture was refluxed for 6 h and then allowed to cool to ambient temperature. 2.7 l of demineralized water were added then acetic acid to adjust the reaction mixture to pH 4.5. The resulting precipitate was filtered, washed with demineralized water (2×600 ml). The solid was triturated in succession with demineralized water (2×4.2 l) and ethanol, (1.5 l), filtered, washed with ethanol (2×300 ml) followed by hexane (2×400 ml) and dried in vacuo at 45° C. to give 127 g (yield: 98%) of 6-chloro-2-mercaptothiazolo[4,5-b]pyridine used without further purification.

1.3 6-Chloro-2-[(3-allyl)thio]thiazolo[4,5-b]pyridine

To a stirred solution of 0.3 g (1.7 mmol) of the thiol from Example 1.2 in 1 ml of dimethylformamide was added a solution of 0.3 g (2.52 mmol) of allylbromide in 1 ml of dimethylformamide and 0.3 g (1.8 mmol) of potassium carbonate. The reaction mixture was stirred at 90° C. for 12 h and then allowed to cool to ambient temperature. 2 ml of demineralized water were added and the mixture was then extracted with dichloromethane. The organic layer was washed with water (2×5 ml), dried over sodium sulfate, filtered and then concentrated in vacuo to yield 0.4 g of the title product.

Example 2

6-Chloro-2-[(3-allylsulfinyl]thiazolo[4,5-b]pyridine

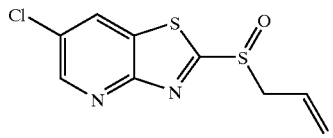

To a solution of 0.03 g (0.1 mol) of 6-chloro-2-[(3-allyl)thio]thiazolo[4,5-b]pyridine from Example 1.3 in 2 ml of a 2:1 mixture of dichloromethane and acetic acid were added 13 ml (0.4 mmol) of a 30% by weight aqueous solution of hydrogen peroxide. The solution was stirred for 12 h at ambient temperature. The reaction solution was diluted with 3 ml of water and then extracted with 4 ml of dichloromethane. The organic layer was washed with 3 ml of an aqueous solution of $Na_2S_2O_4$, dried over sodium sulfate and then concentrated in vacuo to give 0.04 g of the title compound.

Example 3

6-Chloro-2-(methylthio)thiazolo[4,5-b]pyridine

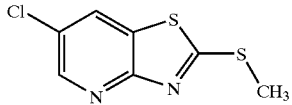

328 g (2.31 mol) of methyl iodide were added dropwise to a stirred suspension of 363 g (2.62 mol) of potassium carbonate and 354 g (1.75 mol) of 6-chloro-2-mercaptothiazolo[4,5-b]pyridine from Example 1.2 in 2.28 l of dimethylformamide at 5° C. The reaction mixture was stirred at ambient temperature for 68 h and then poured into 4.5 l of demineralized water. The precipitate was filtered, rinsed with water (2×500 ml) and then dried in vacuo at 45° C. to give 308.9 g (yield: 81%) of 6-chloro-2-(methylthio)thiazolo[4,5-b]pyridine.

Example 4

6-Chloro-2-(methylsulfonyl)thiazolo[4,5-b]pyridine

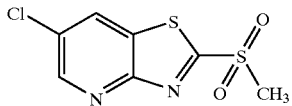

To a solution of 333 g (1.45 mol) 3-chloroperoxybenzoic acid (75% assay) in 2 l of dichloromethane was added a slurry of 120 g (0.55 mol) 6-chloro-2-(methylthio)thiazolo[4,5-b]pyridine from Example 3.1 in 700 ml of dichloromethane in portions over a period of 20 min. The solution was refluxed for 6 h before additon of an additional portion of a solution of 50 g of 3-chloroperoxybenzoic acid in 500 ml dichloromethane. Then the reaction mixture was refluxed for further 2 h. The reaction mixture was allowed to cool to ambient temperature, diluted with dichloromethane (1 l) and then washed with 6 l of a 5% by weight aqueous sodium carbonate solution. The aqueous sodium carbonate layer was extracted with 2 l of dichloromethane. The combined organic layers were washed with 3 l of a saturated aqueous sodium bicarbonate solution followed by 3 l of brine, dried over sodium sulfate, filtered and then concentrated in vacuo to a thick slurry. The residue was taken up in 100 ml of hexane, filtered, washed with 150 ml of a solution of ethyl acetate (20% by volume) in hexane followed by 300 ml of hexane and then dried in vacuo at 45° C. to give 117 g (yield: 85%) of the title compound (m.p. 201–202° C.).

The compounds I-71 to I-156, I-196 to I-255 and I-279 to I-311, listed in Table 1 were prepared in analogues manner.

What is claimed is:

1. A method for controlling harmful fungi, which comprises treating the fungi or materials, plants, soil or seed to be protected against fungal attack with an effective amount of a thiazolo[4,5-b]pyridine of the formula I:

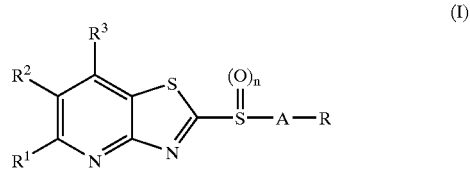

in which the radicals $R^1$, $R^2$, $R^3$, A and the index n have the following meanings:

$R^1$, $R^2$, $R^3$: independently of one another are: hydrogen, halogen, $C_1$–$C_4$-alkyl, $C_1$–$C_4$-alkoxy, $C_1$–$C_4$-haloalkyl, $C_1$–$C_4$-alkoxy-$C_1$–$C_4$-alkyl or phenyl which may be unsubstituted or carry 1, 2, 3 or 4 substituents which are selected, independently of one another, from halogen, nitro, cyano, alkyl, alkoxy, $OCHF_2$ or $CF_3$;

n: 0, 1 or 2;

R: hydrogen, cyano, halogen, $C_1$–$C_6$-alkyl, $C_1$–$C_4$-haloalkyl, $C_1$–$C_4$-alkoxy, $C_2$–$C_4$-alkenyl, $C_2$–$C_4$-haloalkenyl, $C_2$–$C_4$-alkynyl, $C_2$–$C_4$-haloalkynyl, cyano-$C_1$–$C_4$-alkyl, $C_1$–$C_4$-alkoxy-$C_1$–$C_4$-alkyl, $C_3$–$C_8$-cycloalkyl, tris($C_1$–$C_4$-alkyl)silyl, tris($C_1$–$C_4$-alkyl)silyloxy, $COR^4$, $COOR^5$, $CONR^6R^7$, $S(O)_kR^8$, phenyl, phenoxy, a 5 or 6 membered heterocycle, which has 1, 2, or 3 heteroatoms being selected from O, S and N, and which may be saturated, unsaturated or aromatic, wherein phenyl, phenoxy and the heterocycle, independently of each other, may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$; wherein k is 0, 1 or 2;

$R^4$ is hydrogen, $C_1$–$C_6$-alkyl, phenyl and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

$R^5$ is $C_1$–$C_6$-alkyl, $C_1$–$C_4$-alkoxy-$C_1$–$C_4$-alkyl, phenyl and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

$R^6$, $R^7$ independently from one another are hydrogen, $C_1$–$C_6$-alkyl, $C_1$–$C_4$-alkoxy-$C_1$–$C_4$-alkyl, phenyl, and phenyl-$C_1$–$C_4$-alkyl, wherein phenyl and phenyl-$C_1$–$C_4$-alkyl may carry 1, 2, 3 or 4 substituents on the phenyl ring, which are selected, independently of one another, from halogen, nitro, cyano, $C_1$–$C_4$-alkyl, $C_1$–$C_4$-alkoxy, $OCHF_2$ or $CF_3$; or may together form a 5- or 6-membered heterocycle, which may additionally to the nitrogen atom may have 1 or 2 further heteroatoms selected from N, O or S, $R^8$ is $C_1$–$C_6$-alkyl, $C_1$–$C_4$-haloalkyl, phenyl, and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

A: $C_1$–$C_4$-alkylene; or

A—R: may together be dihalomethyl, trihalomethyl, $C_3$–$C_8$-cycloalkyl, $C_2$–$C_4$-alkenyl, $C_2$–$C_4$-haloalkenyl, $C_5$–$C_8$-cycloalkenyl or a 5 or 6 membered heterocycle, which has 1, 2, or 3 heteroatoms being selected from O, S and N, which may be saturated, unsaturated or aromatic, and which may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$, wherein cycloalkyl and cycloalkenyl, may independently carry 1, 2, 3 or 4 substituents, which are selected, independently of one another, from halogen and $C_1$–$C_4$-alkyl, and/or may contain a carbonyl or thiocarbonyl ring member;

and/or with an agricultural acceptable salt thereof.

2. A method as claimed in claim 1, where the radical $R^2$ in formula I is different from hydrogen.

3. A method as claimed in claim 1, where the radicals $R^1$ to $R^3$ in formula I are as defined below;

$R^1$ hydrogen or $C_1$–$C_4$-alkyl;

$R^2$ hydrogen, halogen, $C_1$–$C_4$-alkyl, $C_1$–$C_4$-haloalkyl;

$R^3$ hydrogen.

4. A method as claimed in claim 1, where A in formula I is methylene, 1,2-ethylene, 1,1-ethylene or 1,3-propylene and R is phenyl, phenoxy, a 5 or a 6 membered heterocycle, which has 1, 2, or 3 heteroatoms being selected from O, S and N, wherein phenyl, phenoxy and the heterocycle, independently of each other, may be unsubstituted or substituted as defined above.

5. A method as claimed in claim 1, where A in formula I is methylene, 1,2-ethylene, 1,1-ethylene or 1,3-propylene and R is selected from cyano, $C_1$–$C_4$-alkoxy, cyano-$C_1$–$C_4$-alkyl, $C_1$–$C_4$-alkoxy-$C_1$–$C_4$-alkyl, tris($C_1$–$C_4$-alkyl)silyl, tris($C_1$–$C_4$-alkyl)silyloxy, $COR^4$, $COOR^5$, $CONR^6R^7$ or $S(O)_kR^8$, wherein the radicals $R^4$ to $R^9$ and the integer k are defined as above.

6. An agricultural composition in form of a directly sprayable solution, powder, suspension, dispersion, emulsion, emulsion concentrate, oil dispersion, paste, dust, a material for spreading, or in the form of granules, comprising at least one agriculturally acceptable liquid or solid carrier, and a fungicidally effective amount of at least one thiazolo[4,5-b]pyridine of formula I

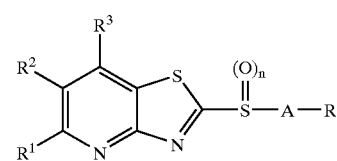

wherein
$R^1$, $R^2$, $R^3$ are independently of one another hydrogen, halogen, $C_1$–$C_4$-alkyl, $C_1$–$C_4$-alkoxy, $C_1$–$C_4$-haloalkyl, $C_1$–$C_4$-alkoxy-$C_1$–$C_4$-alkyl or phenyl which may be unsubstituted or carry 1, 2, 3 or 4 substituents which are selected, independently of one another, from halogen, nitro, cyano, alkyl, alkoxy, $OCHF_2$ or $CF_3$;

n is 1 or 2;

R is hydrogen, cyano, halogen, $C_1$–$C_6$-alkyl, $C_1$–$C_4$-haloalkyl, $C_1$–$C_4$-alkoxy, $C_2$–$C_4$-alkenyl, $C_2$–$C_4$-haloalkenyl, $C_2$–$C_4$-alkynyl, $C_2$–$C_4$-haloalkynyl, cyano-$C_1$–$C_4$-alkyl, $C_1$–$C_4$-alkoxy-$C_1$–$C_4$-alkyl, $C_3$–$C_8$-cycloalkyl, tris($C_1$–$C_4$-alkyl)silyl, tris($C_1$–$C_4$-alkyl)silyloxy, $COR^4$, $COOR^5$, $CONR^6R^7$, $S(O)_kR^8$, phenyl, phenoxy, a 5 or 6 membered heterocycle, which has 1, 2, or 3 heteroatoms being selected from O, S and N, and which may be saturated, unsaturated or aromatic, wherein phenyl, phenoxy and the heterocycle, independently of each other, may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$; wherein k is 0, 1 or 2;

$R^4$ is hydrogen, $C_1$–$C_6$-alkyl, phenyl and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

$R^5$ is $C_1$–$C_6$-alkyl, $C_1$–$C_4$-alkoxy-$C_1$–$C_4$-alkyl, phenyl and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

$R^6$, $R^7$ independently from one another are hydrogen, $C_1$–$C_6$-alkyl, $C_1$–$C_4$-alkoxy-$C_1$–$C_4$-alkyl, phenyl, and phenyl-$C_1$–$C_4$-alkyl, wherein phenyl and phenyl-$C_1$–$C_4$-alkyl may carry 1, 2, 3 or 4 substituents on the phenyl ring, which are selected, independently of one another, from halogen, nitro, cyano, $C_1$–$C_4$-alkyl, $C_1$–$C_4$-alkoxy, $OCHF_2$ or $CF_3$; or may together form a 5- or 6-membered heterocycle, which may additionally to the nitrogen atom may have 1 or 2 further heteroatoms selected from N, O or S;

$R^8$ is $C_1$–$C_6$-alkyl, $C_1$–$C_4$-haloalkyl, phenyl, and phenyl-$C_1$–$C_4$-alkyl, wherein phenyl and phenyl-$C_1$–$C_4$-alkyl may carry 1, 2, 3 or 4 substituents on the phenyl ring which are selected, independently of one another, from halogen, nitro, cyano, $C_1$–$C_4$-alkyl, $C_1$–$C_4$-alkoxy, $OCHF_2$ or $CF_3$;

A is $C_1$–$C_4$-alkylene; or

A—R are together dihalomethyl, trihalomethyl, $C_3$–$C_8$-cycloalkyl, $C_2$–$C_4$-alkenyl, $C_2$–$C_4$-haloalkenyl, $C_5$–$C_8$- cycloalkenyl or a 5 or 6 membered heterocycle, which has 1, 2, or 3 heteroatoms being selected from O, S and N, which may be saturated, unsaturated or aromatic, and which may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$, wherein cycloalkyl and cycloalkenyl, may independently carry 1, 2, 3 or 4 substituents, which are selected, independently of one another, from halogen and $C_1$–$C_4$-alkyl, and/or may contain a carbonyl or thiocarbonyl ring member;

and/or at least one agriculturally acceptable salt thereof.

7. The composition defined in claim 6, wherein the radical $R^2$ in formula I is different from hydrogen.

8. The composition defined in claim 6, wherein $R^1$ is hydrogen or $C_1$–$C_4$-alkyl;

$R^2$ is hydrogen, halogen, $C_1$–$C_4$-alkyl or $C_1$–$C_4$-haloalkyl; and $R^3$ is hydrogen.

9. An agricultural composition in form of a directly sprayable solution, powder, suspension, dispersion, emulsion, emulsion concentrate, oil dispersion, paste, dust, a material for spreading, or in the form of granules, comprising a fungicidally effective amount of at least one thiazolo[4,5-b]pyridine of formula I

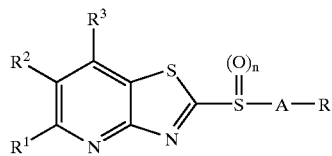

wherein $R^1$, $R^2$, $R^3$ are independently of one another: hydrogen, halogen, $C_1$–$C_4$-alkyl, $C_1$–$C_4$-alkoxy, $C_1$–$C_4$-haloalkyl, $C_1$–$C_4$-alkoxy-$C_1$–$C_4$-alkyl or phenyl which may be unsubstituted or carry 1, 2, 3 or 4 substituents which are selected, independently of one another, from halogen, nitro, cyano, alkyl, alkoxy, $OCHF_2$ or $CF_3$;

n is 0;

A is methylene, 1,2-ethylene, 1,1-ethylene or 1,3-propylene; and

R is phenyl, phenoxy, a 5 or 6 membered heterocycle, which has 1, 2, or 3 heteroatoms being selected from O, S and N, and which may be saturated, unsaturated or aromatic, wherein phenyl, phenoxy and the heterocycle, independently of each other, may carry 1, 2, 3 or 4 substituents which are selected, independently of one another, from halogen, nitro, cyano, $C_1$–$C_4$-alkyl, $C_1$–$C_4$-alkoxy, methylsulfonyl, $OCHF_2$, $CF_3$ or phenyl, which may carry 1, 2 or 3 radicals selected from halogen, $C_1$–$C_4$-alkyl, methylsulfonyl, $OCHF_2$ or $CF_3$;

or an agriculturally acceptable salt thereof, and at least one agriculturally acceptable liquid or solid carrier.

10. The composition defined in claim 9, wherein R is phenyl, phenoxy, a 5 or 6 membered heterocycle, which has 1, 2, or 3 heteroatoms being selected from O, S and N, and which may be saturated, unsaturated or aromatic, wherein phenyl, phenoxy and the heterocycle, independently of each other, may carry 1, 2, 3 or 4 substituents which are selected, independently of one another, from halogen and $C_1$–$C_4$-alkyl.

11. The composition defined in claim 9, wherein the radical $R^2$ in formula I is different from hydrogen.

12. The composition defined in claim 9, wherein $R^1$ is hydrogen or $C_1$–$C_4$-alkyl;

$R^2$ is hydrogen, halogen, $C_1$–$C_4$-alkyl or $C_1$–$C_4$-haloalkyl; and $R^3$ is hydrogen.

* * * * *

UNITED STATES PATENT AND TRADEMARK OFFICE
CERTIFICATE OF CORRECTION

PATENT NO. : 6,914,068 B2  Page 1 of 1
APPLICATION NO. : 09/902783
DATED : July 5, 2005
INVENTOR(S) : Haley et al.

It is certified that error appears in the above-identified patent and that said Letters Patent is hereby corrected as shown below:

Title page, under (*) Notice
The phrase, "This patent is subject to a terminal disclaimer," should be deleted from the face of the patent.

Signed and Sealed this

Twenty-second Day of May, 2007

JON W. DUDAS
*Director of the United States Patent and Trademark Office*